US00PP15216P2

(12) United States Plant Patent
Scorza

(10) Patent No.: US PP15,216 P2
(45) Date of Patent: Oct. 12, 2004

(54) PEACH TREE NAMED 'CRIMSON ROCKET'

(50) Latin Name: *Prunus persica*
Varietal Denomination: Crimson Rocket

(75) Inventor: Ralph Scorza, Shepherdstown, WV (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/984,541

(22) Filed: Oct. 30, 2001

(51) Int. Cl.[7] ..... A01H 5/00
(52) U.S. Cl. ..... Plt./198
(58) Field of Search ..... Plt./198

*Primary Examiner*—Anne Marie Grunberg
(74) *Attorney, Agent, or Firm*—John D. Fado; Evelyn M. Rabin

(57) ABSTRACT

A new and distinct variety of peach called 'Crimson Rocket' is characterized by a narrow, columnar growth form suitable for high-density plantings, home gardens and ornamental purposes. Fruit is yellow, melting-flesh of excellent dessert-quality flavor, and of medium to large size with approximately 80% red blush over a yellow ground color.

3 Drawing Sheets

BACKGROUND OF THE NEW VARIETY

The present invention relates to a new and distinct variety of columnar peach tree [*Prunus persica* (L.) Batsch] which is named 'Crimson Rocket'.

The new variety is attractive commercially for its narrow columnar canopy, productivity and for fruit of excellent quality. The tree is suitable for high-density plantings, home garden and ornamental purposes.

Columnar trees were first reported from Japan where they had been developed as ornamentals. Fruit quality of the original columnar trees (also known as "pillar" or "broomy" trees) was very poor. Breeding programs were thus begun in order to improve fruit quality. The new variety was originated at the Appalachian Fruit Research Station, Agricultural Research Service, U.S. Department of Agriculture in Kearneysville, W. Va. and was identified as KV930455. It resulted from hand pollination of peach seedling identified as KV881465 (unpatented) with pollen from peach MA6-1-90 (unpatented). KV881465 resulted from hand pollination of 'Flavortop' nectarine (unpatented) with pollen of "pillar" peach. MA6-1-90 was a seedling from a cross of ('Suncrest'×K2, unpatented)×"pillar". The "pillar" pollen used in these crosses was obtained from Italy and is not patented. MA6-1-90 was obtained from the Instituto Sperimentale per la Frutticoltura, Forli, Italy.

The new variety was selected in 1996 from a group of 77 seedlings produced from the pollination described hereinabove. The original 'Crimson Rocket' tree has maintained its columnar form, high fruit quality and productivity for 6 years. Buds of 'Crimson Rocket' were grafted onto 'Lovell', a widely used rootstock of standard tree growth habit, following standard bud-grafting techniques. Following one year of growth in the nursery, these grafted trees were dug and transferred to their permanent orchard location following standard techniques. A total of 96 bud-grafted 'Crimson Rocket' trees were planted in a replicated block orchard design with 12 treatment blocks, each containing 8 trees. Trees were spaced at 1.5 m, 2 m, 4 m or 6 m within rows, and 6 m between rows. Half of the trees were pruned to one leader (one major limb) and half to multi-leader (3 major limbs). These trees were tested in this planting for 3 years and have maintained their tree form, high fruit quality and productivity. Shoots of 'Crimson Rocket' were collected and rooted following standard procedures. Trees developed from these rooted cuttings and grown in a greenhouse for 2 years have maintained the columnar growth habit. No aberrant types have appeared in any of these plantings developed through vegetative propagation, demonstrating the stability of the new variety.

The new variety is distinct from its parents in its combination of high fruit quality and columnar growth habit. Both parents were upright but not columnar, with fruit of moderate quality. It is distinguished from its parents as well as other peach varieties by a distinctly columnar growth habit with branch angles from the main axis at approximately 35–40°, in contrast to branch angles of standard peach trees which average approximately 60° and upright trees which average approximately 42–51°.

Fruit are melting-flesh, dessert type. Fruit flesh is yellow, flavorful and firm until full-ripe. Fruit have yellow ground color with red blush that covers approximately 80% of the fruit surface. Fruit size averages 69–72 mm in diameter and 179 g in weight. Fruit are sweet with a good balance of acidity. Brix of firm-ripe fruit averages between 11.5 and 13°, depending on date of harvest. Fruit maintains firmness on the tree and in storage at levels comparable to commercial peach cultivars.

SUMMARY OF THE INVENTION

The new and distinct variety of peach tree is productive and vigorous with a narrow columnar growth habit. The fruit is medium to large in size and of excellent dessert-quality flavor. The fruit has yellow melting-flesh with approximately 80% red blush over a yellow ground cover.

Figure 1:
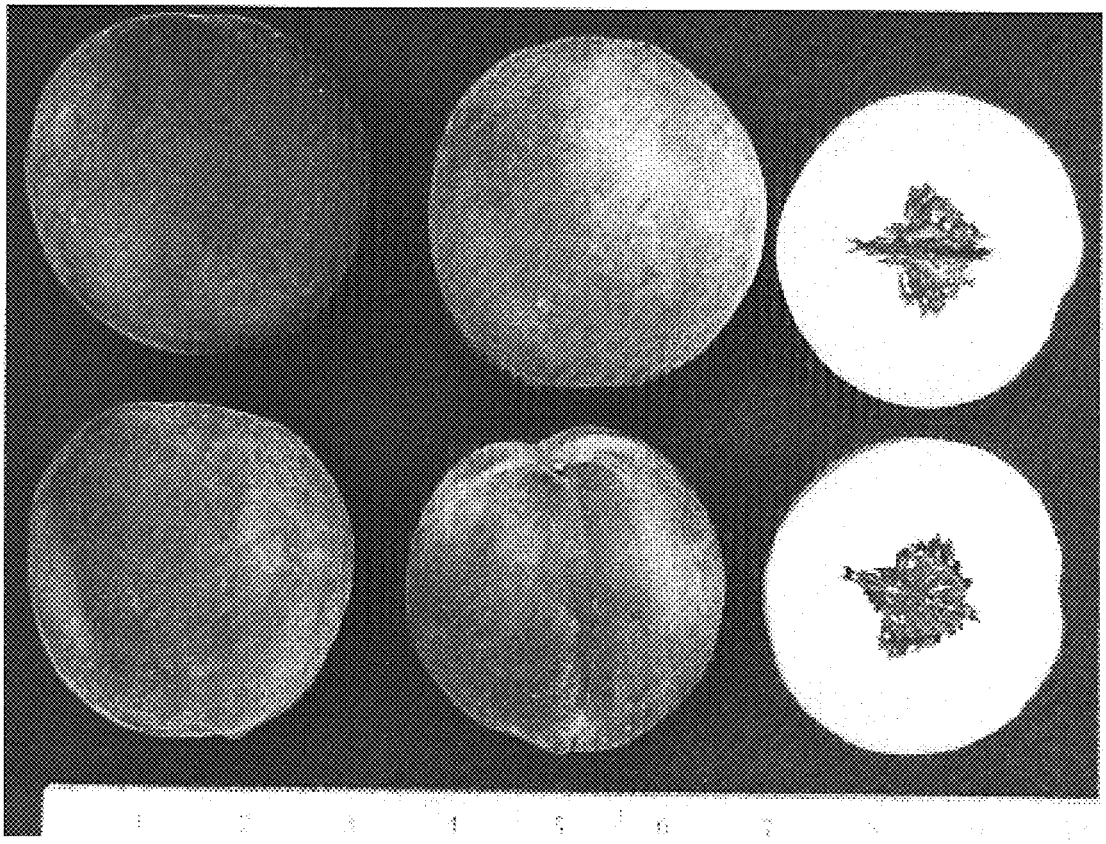
FIG. 1 is a photograph of the fruit of 'Crimson Rocket' peach in full color showing the ripe fruit viewed in profile and sectioned in half from end to end, with one one-half of the fruit shown with the stone in place in the flesh.
Figure 2:
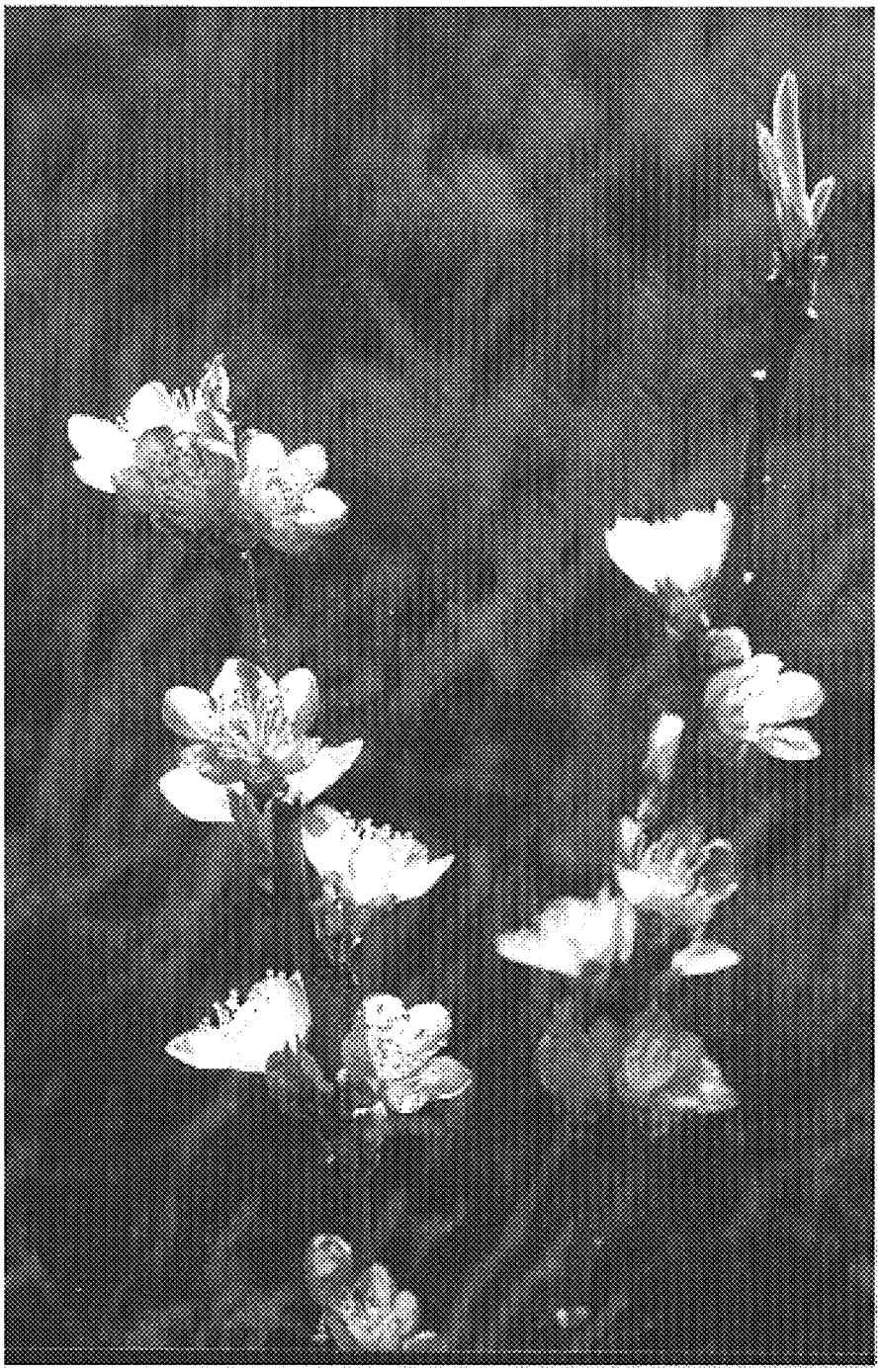
FIG. 2 is a photograph of representative stems of 'Crimson Rocket' peach flowers in full color.
Figure 3:
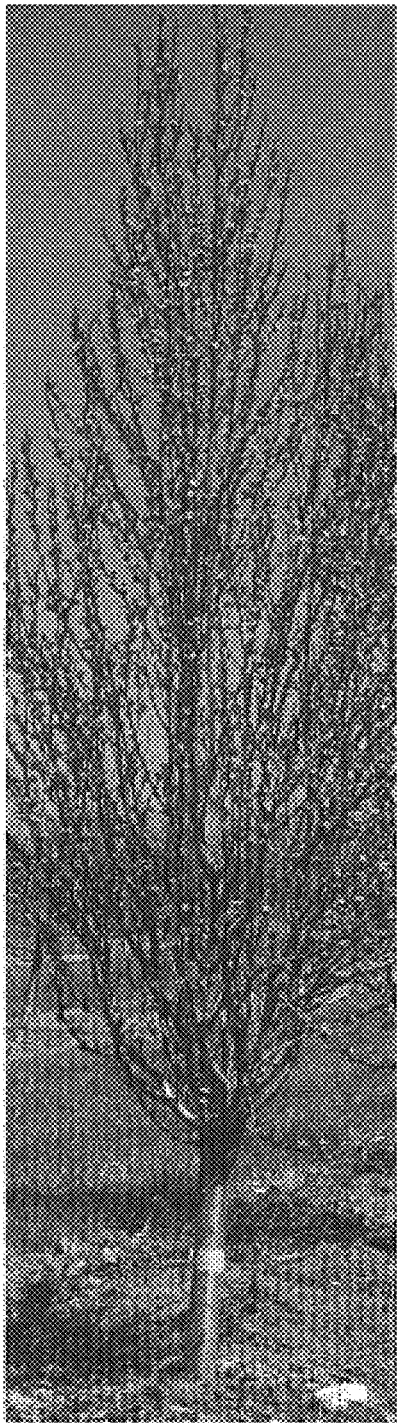
FIG. 3 is a photograph of a tree of 'Crimson Rocket' peach in flower, grafted on the 'Lovell' seedling rootstock, after 2 growing seasons, showing columnar form of tree architecture.

The figures show photographs in color as accurate as reasonably possible to attain in color photographic reproductions of this type.

DETAILED DESCRIPTION OF THE NEW VARIETY

The following is a detailed description of the botanical and pomological characteristics of the subject peach. Color data are presented in Royal Horticultural Society (R.H.S.) Colour Chart designations. Where dimensions, sizes, color and other characteristics are given, it is to be understood that such characteristics are approximations of averages set forth as accurately as practicable.

The descriptions reported herein are from specimens grown at Kearneysville, W. Va.

Tree:

*Size/vigor.*—Canopy size at 2 years — height 3.1 m, width 1.3 m, depth 1.2 m compared with a standard tree ('Harrow Beauty') control at 2.8, 2.1 and 2.3 m, respectively; average 36 cm of seasonal shoot growth from previous season growth on 5 year-old trees.

*Growth.*—Columnar, narrow canopy; branch angles from the main axis at approximately 35–40°.

*Density.*—Medium dense to dense.

*Productivity.*—After 2 years in the field, 0.5 kg fruit/tree compared with control 'Harrow Beauty' at 1.2 kg/tree.

*Bearing.*—Regular; no alternate bearing noted.

*Disease resistance.*—Not determined.

Trunk:

*Size.*—Circumference 18.4 cm at 2 years on 'Lovell' rootstock compared with standard tree ('Harrow Beauty') at 19.6.

*Color.*—Ranging from RHS 201 B to C.

*Trunk lenticel density.*—6/mm$^2$.

*Trunk lenticel color.*—167C.

*Trunk lenticel size.*—7 mm long.

Branches:

*Size.*—One-year branch diameter 11.9 mm; 2-year branch diameter 18.0 mm.

*Texture.*—Smooth to medium rough; varies with maturity.

*Color.*—RHS 166B.

*Branch crotch angles from trunk.*—~35–40°.

Leaves:

*Size.*—Medium; average length 14.1 cm, average width 3.6 cm.

*Texture.*—Glabrous.

*Margin.*—Crenate to serrulate.

*Form.*—Lancelolate, pointed.

*Petiole.*—Length — 9.5 mm; width — 1.7 mm; thickness — 1.6 mm; color RHS 137C.

*Glands.*—Reniform; located on base of leaf and upper portion of the petiole; length — 1.1 mm; average 4/leaf varying from 1–7.

*Color.*—Upper surface RHS 137B; lower surface RHS 137C.

Flowers:

*Size.*—Petals 13 mm long×11 mm wide.

*Bloom period.*—Variable depending on weather, late March to mid-April in the Eastern Panhandle of West Virginia.

*Color.*—Ranging from RHS N74 A to D; anthers RHS 16A.

*Pollen.*—Present; self-fertile, no pollinator required; color RHS 16B.

*Pistils.*—One.

*Description.*—Flowers are complete, perfect, perigynous; sepals (5) form a hypanthium cup; petals (5) are attached to hypanthium; stamens are attached to interior of hypanthium at or below the rim of the hypanthium cup; pistil (1) is superior averaging; no scent is detectable.

Fruit:

*Maturity when described.*—Shipping ripe to eating ripe.

*Average date of harvest.*—Late July to early August in Kearneysville, W. Va.

*Size.*—Medium to large; average diameter axially 69–72 mm; weight 170 g and can vary based on crop load and environment.

*Fruit pedicel color.*—RHS 145A.

*Use.*—Dessert.

*Market.*—Local and long distance.

Flesh:

*Ripens.*—Evenly.

*Texture.*—Melting flesh.

*Firmness.*—Slope of rate of softening over 14 days using electronic impact sensor[1] −0.60 compared with −0.62 for standard cultivar 'O'Henry' ([1]Meredith et al. 1990, *Transactions ASAE,* vol. 33, pp. 186–188).

*Fibers.*—Small, few, tender.

*Juice.*—Moderate.

*Aroma.*—Moderate.

*Eating quality.*—Very good; brix of firm-ripe fruit averages between 11.5 and 13°, depending on maturity at harvest.

*Flesh color.*—15D.

*Pit cavity color.*—Ranging from RHS 26A to 26B; proximal to the stone RHS 46A to RHS 53A.

Skin:

*Tendency to crack.*—None.

*Down.*—Moderate; short in length.

*Skin color.*—Blush (overcolor) ranging from RHS N77A to RHS 34B to RHS 34C; ground (undercolor) RHS 11B.

Stone:

*Type.*—Freestone.

*Size.*—Medium; average length 37.6 mm, average width 29.8 mm, average thickness 21.4 mm.

*Form.*—Obovate.

*Tendency to split.*—Two—7% stone splitting depending on environmental conditions.

*Color.*—RHS 175A.

I claim:

1. A new and distinct variety of peach tree, substantially as illustrated and described.

* * * * *